(12) United States Patent
Yousefian (10) Patent No.: US 12,274,596 B1
(45) Date of Patent: Apr. 15, 2025

(54) FACE AND AIRWAY DEVELOPER APPLIANCE AND METHOD

(71) Applicant: Joseph Yousefian, Bellevue, WA (US)

(72) Inventor: Joseph Yousefian, Bellevue, WA (US)

( * ) Notice: Subject to any disclaimer, the term of this patent is extended or adjusted under 35 U.S.C. 154(b) by 628 days.

(21) Appl. No.: 16/729,551

(22) Filed: Dec. 30, 2019

Related U.S. Application Data (60) Provisional application No. 62/843,089, filed on May 3, 2019.

(51) Int. Cl.
*A61C 7/06* (2006.01)
*A61C 7/36* (2006.01)
*A61F 5/56* (2006.01)

(52) U.S. Cl.
CPC ............... *A61C 7/06* (2013.01); *A61C 7/36* (2013.01); *A61F 5/56* (2013.01); *Y10S 602/902* (2013.01)

(58) Field of Classification Search
CPC .. A61C 7/06; A61C 7/065; A61C 7/08; A61C 7/10; A61C 7/36; A61C 7/00; A61F 5/56; A61F 5/566; A61F 5/58; A61B 17/24; Y10S 602/902; A61N 2005/00645; A61N 2005/0647; A61N 2005/0645
USPC .......................................................... 433/5–6
See application file for complete search history.

(56) References Cited

U.S. PATENT DOCUMENTS

| | | | | |
|---|---|---|---|---|
| 2,334,894 A | * | 11/1943 | Atkinson | A61C 7/06 D24/180 |
| 3,512,257 A | * | 5/1970 | Stifter | A61C 7/06 433/5 |
| 4,988,291 A | | 1/1991 | Grummons | |
| 5,158,451 A | | 10/1992 | Pourcho | |
| 6,976,838 B1 | | 12/2005 | Keles | |
| 7,121,824 B2 | | 10/2006 | Keles | |
| 8,529,252 B2 | | 9/2013 | Bukhary | |
| 8,821,155 B2 | | 9/2014 | Mitani | |
| 9,216,103 B2 | * | 12/2015 | Kim-Berman | A61B 17/24 |
| 2010/0294283 A1 | * | 11/2010 | Li | A61F 5/566 128/848 |
| 2015/0230970 A1 | * | 8/2015 | Kaner | A61F 5/566 128/848 |

(Continued)

OTHER PUBLICATIONS mayoclinic.org—sleep apnea (Year: 2022).*
Simple Machines—Levers _ Let's Talk Science (Year: 2023).*

*Primary Examiner* — Victoria Hicks Fisher
(74) *Attorney, Agent, or Firm* — Kolitch Romano Dascenzo Gates LLC (57) ABSTRACT

A facemask and accessories which overcomes the adverse effects and limitations of current designs by moving the maxilla and mandible in forward direction, which assists in correcting maxillary and mandibular skeletal and dentoalveolar deficiency and help expand the upper airway by advancing the mandible. This is accomplished by a design that is supported only by forehead and produces forces in front of maxilla and mandible. The extra-oral facebow design is characterized by providing two independent force adjustments, one above the forehead and the other one in front of the face by attachments to the upper and lower jaw bones and teeth. In particular, the two independent adjustments are provided by a fully adjustable forehead pad and bilateral adjustable bows on opposite sides of the facebow's extra-oral frame to provide protracting forces.

13 Claims, 11 Drawing Sheets

(56) References Cited

U.S. PATENT DOCUMENTS

| | | | |
|---|---|---|---|
| 2021/0145468 A1* | 5/2021 | Kass | A61B 17/24 |
| 2021/0205119 A1* | 7/2021 | De Clerck | A61F 5/566 |

\* cited by examiner

FACE AND AIRWAY DEVELOPER APPLIANCE AND METHOD

RELATED APPLICATIONS

This application claims benefit of provisional patent application Ser. No. 62/843,089, filed May 3, 2019, which is incorporated by reference as if fully set forth herein.

BACKGROUND

Orthodontists, dental practitioners and medical-dental researchers are constantly searching for new and improved ways to correct the problem of short and small jaws that can contribute to an unaesthetic facial appearance and the development of airway related disorders such as obstructive sleep apnea. This condition, by a narrowing of the tongue space and a retraction of the tongue back to the airway can cause the constriction of the upper airway in the retropalatal (behind the palate), retroglossal (behind the tongue) and hypoglossal (behind and below the tongue) areas. As a result, this condition not only causes unaesthetic small and retruded jaws and adversely affects the facial profile, but also causes the upper airway of the patient to become constricted and thereby resist air passage especially during the deeper stage of sleep when the upper airway muscles relax and cannot provide ideal support for the patency of the airway.

In the past, many different methods have been used in order to address retruded jaws and their effect on the airway. One method that has been utilized by orthodontic practitioners is that of dental expansion of the upper and lower dental arch, combined with dental and/or orthopedic expansion of the upper jaw in transverse direction, followed by forward protraction of the upper and lower jaws by a reverse pull facemask. In this protocol, the face mask utilizes the anchorage from different areas of the face including the combination of the patient's forehead and chin (transferring the force to the body of the mandible and to the temporomandibular joints (TMJ) which are growth sites or centers in children and adolescents still growing [henceforth, "children"]), forehead and zygomatic processes which consists of zygomatic bones and maxillary bone supporting the midface and upper airway of the patient.

The forehead is a stable structure that cannot receive an adverse effect on its growth. However, the use of zygomatic bones or chin can have deleterious effect on the growth and development of these components, especially maxillary and mandibular bones that are attached to them, which can stop or slow down the growth of the upper and lower jaws in children.

In children, force application to the chin by reverse-pull headgear causes downward and backward rotation of the mandible. Although the retrusive forces being applied by the chin cup can benefit a prognathic mandible, it may be detrimental to the TMJ as well as increase open bite tendencies.

SUMMARY OF THE INVENTION

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

The appliance and method of this invention is distinguished from conventional facemasks by avoiding pressure on the zygomatic, maxillary and mandibular bones and TMJs. This invention is characterized by providing extra oral forces supported by the forehead of the patient to pull maxillary and mandibular bones, dentition, and tongue forward and as result help to grow the upper and lower jaw structures also open the airway of the patient by connection to the lower jaw of the patient.

This face and airway developer design and method according to the invention overcomes the adverse effects and limitations of current designs by avoidance of transferring anchorage forces to the zygomatic, maxillary, mandibular and TMJ structures and helps pulling the maxillary, mandibular bones and dentition effectively forward to enlarge the retropalatal, retroglossal and hypoglossal airways.

This is accomplished using a design that positions a pad over the forehead of patient as forehead rest and attached to the frame as type 1 lever system that on one end above the forehead attached to the back of the skull for anchorage by adjustable or fixed, non-elastic or elastic straps that produces forces that transferred over the fulcrum to the other end of the frame and lever in front of the face or mouth of the patient. From this point of attachment, elastics, non-elastic straps or attractive magnetic elements can be extended to the upper and lower jaws by means of brackets, bands attached to the teeth, or via clear aligners, face bows, expanders, bone implants, soft tissue anchors secure to the maxillary and mandibular teeth or bones or tongue.

The device can include an intra-oral frame adapted to be connected to the patient's teeth and an extra-oral frame connected at one end to the intra-oral frame or other connections and connected at the other end to the frame that extend to the forehead rest or face bow attached to it connected via elastic or non-elastic means to the back of the head. The extra-oral design of the invention is characterized by providing adjustments (forehead width and horizontal/vertical dimensions) that allow the invention to be customized to each patient. In particular, the two independent adjustments are provided, one by elastics or non-elastic straps secured above the forehead extended directly or via a face bow frame around the base or back of the patient's head. The other one to the lever arm in front of the face and mouth that is connected intraorally to the teeth or bones or tongue of patient.

This is accomplished using a design that produces forces above the center of resistance of the maxilla and parallel to the Frankfort horizontal plane.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF PREFERRED EMBODIMENTS

Definition: the term "teeth" as used in this application encompasses implants, and any other structure that can deliver a force to the jaw bones, such as an implanted anchor for a mating element.

The term "child" refers to patients whose facial features are still experiencing growth and encompasses adolescents who are still growing.

A "strap" is any element capable of being placed into tension, and thereby to transfer a pulling force. A "strap" may be elastic or inelastic.

An "intra-oral feature" of a patient, is the teeth, as defined above, or the jaws or tongue.

Figure 1:
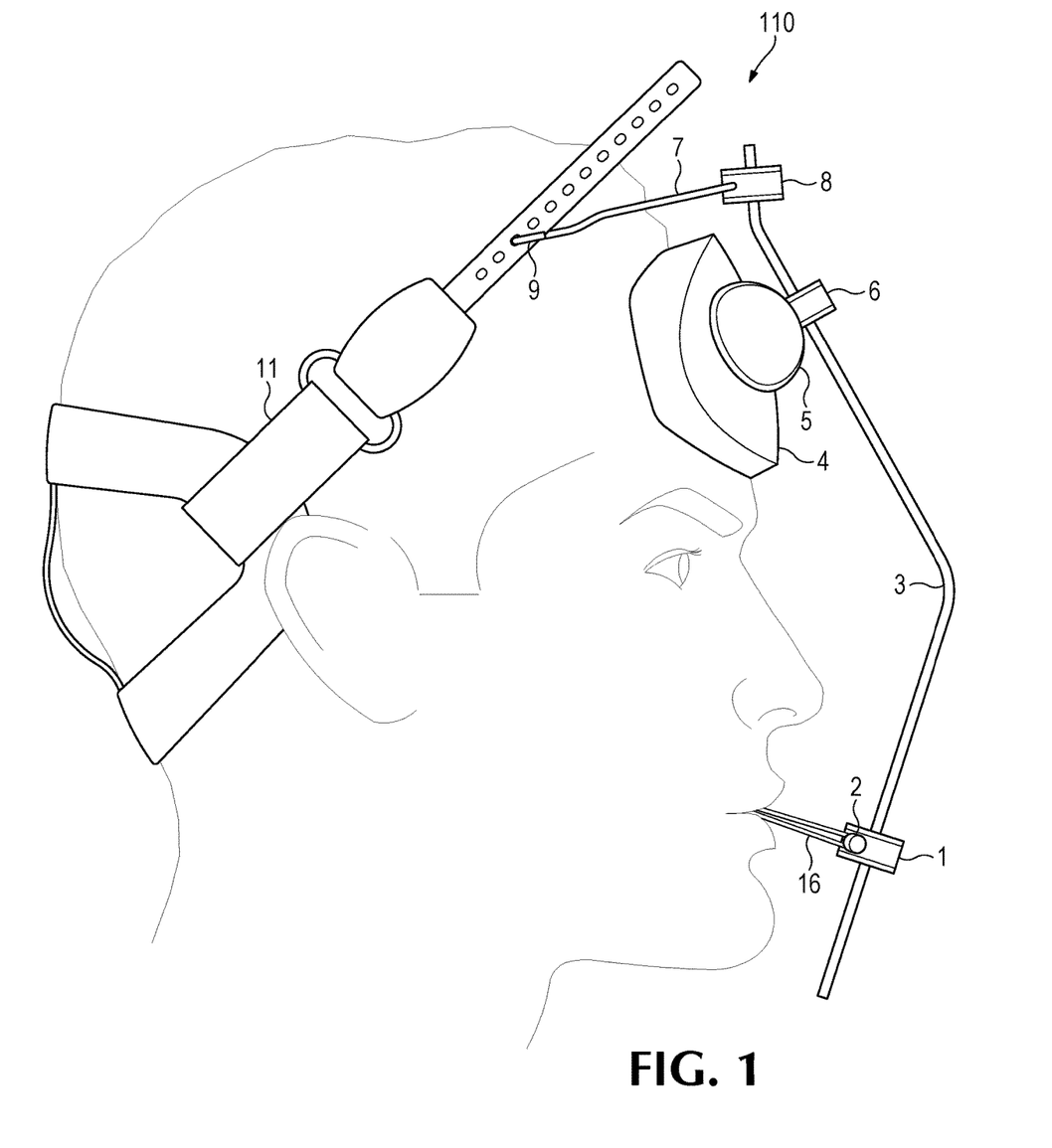
FIG. 1 is a side elevational view of a face and airway developer appliance, according to the present invention, installed onto the face of a human patient, showing the extra-oral portion of the appliance.

Referring to FIG. 1, a face and airway developer appliance 110, includes an extra-oral assembly that consists of a lever 3 in the form of a vertical, bow-shaped metal rod, slidingly engaged to a fulcrum block 6 that is supported by a detachable fulcrum support 5. The fulcrum support 5 is supported solely by cushions 4 contacting the patient's forehead. The appliance includes a bottom block 1, slidingly supported on lever 3 in front of a patient's mouth, which in turn supports a tooth-pull bar 2, for attachment via tooth straps 16 to a patient's intra-oral features.

One embodiment has a lever-pull bow 7 connected to the lever 3 by a top block 8 which pulls the top of lever 3 toward the forehead, causing bar 2 to be pushed away from the jaws. Block 8 can slide on lever 3, to permit proper moment arm force delivery to the lever 3. The bow 7 which extends laterally to the either side of patent's forehead, ends with hooks 9 for connection to a set of head straps 11 that extend on either side of the face of the patient and around the back of the patient's skull. Strap set 11 is adjusted to pull on hooks 109, and thereby pull back on lever 3.

The adjustment blocks 1, 6, 8 permit customization to each patient, as they can each be slid up or down the lever 3 to adjust the force delivery from straps 11.

Figure 2:
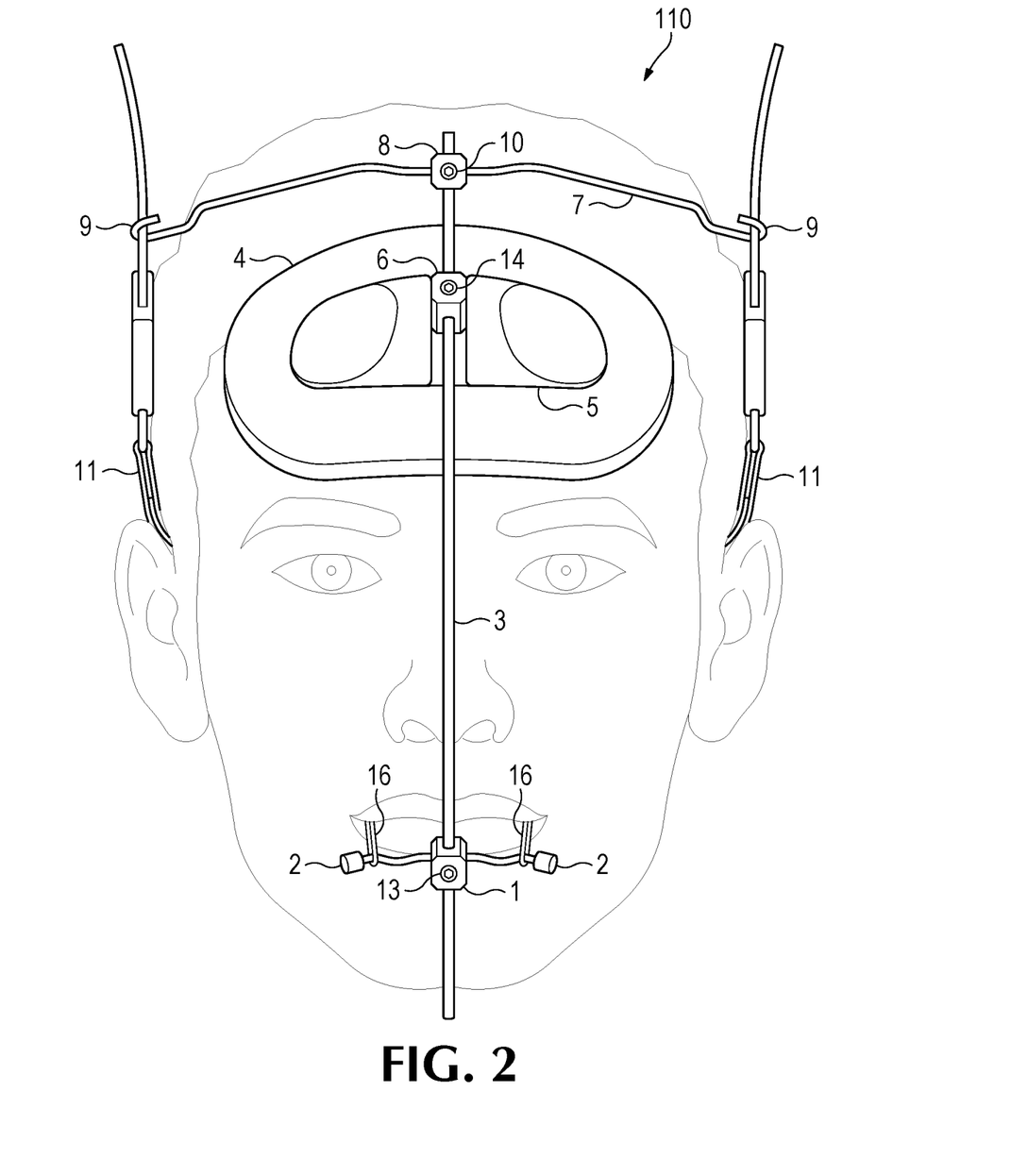
FIG. 2 is a front elevational view of the appliance of FIG. 1, also shown installed onto the face of a human patient.
Figure 3:
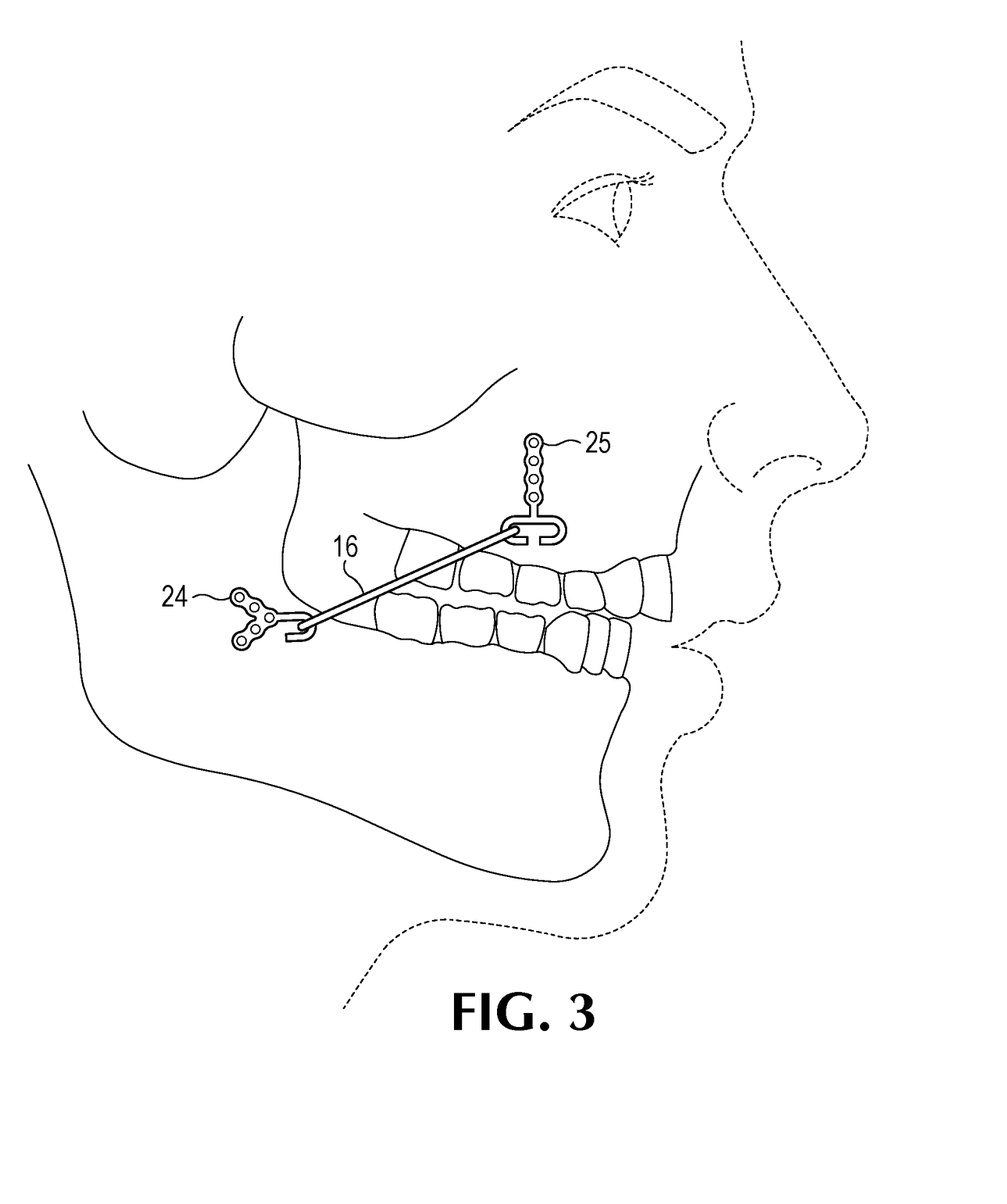
FIG. 3 is a plan side view showing an alternative apparatus for correcting malocclusion and growing the lower jaw.

A set screw 13, 10, 14 (FIG. 2) in block 1, 6, 8 respectively, are used to fix the vertical location of the bar 2 and bow 7 and fulcrum support 5 on the lever 3.

Figure 4A:
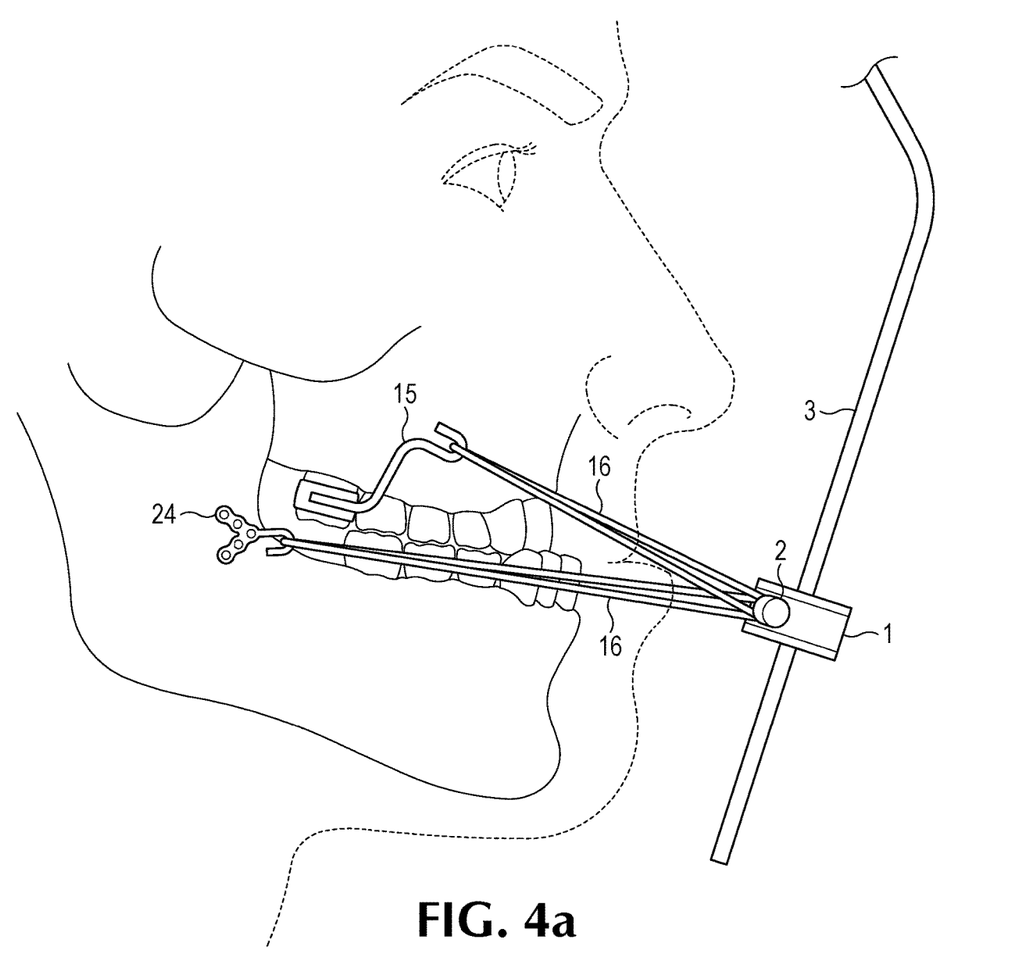
FIG. 4a is a plan side view of a portion of the face and airway developer of FIG. 1, showing the intraoral portion of one embodiment, in its environment attached inside a patient's mouth.
Figure 4B:
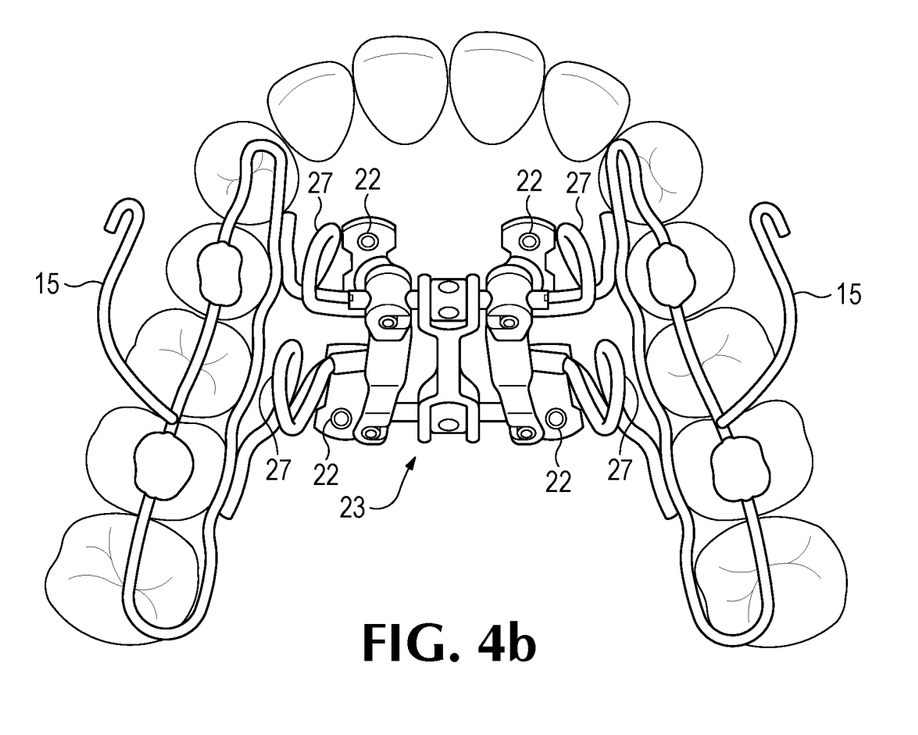
FIG. 4b is a bottom view of a maxillary expander with flexible loops and non-parallel expansion screws attached to the roof of the mouth by mini-implants and bonded to the top of the teeth; and having extension arms to attach to the assembly of FIG. 1 with straps.
Figure 5:
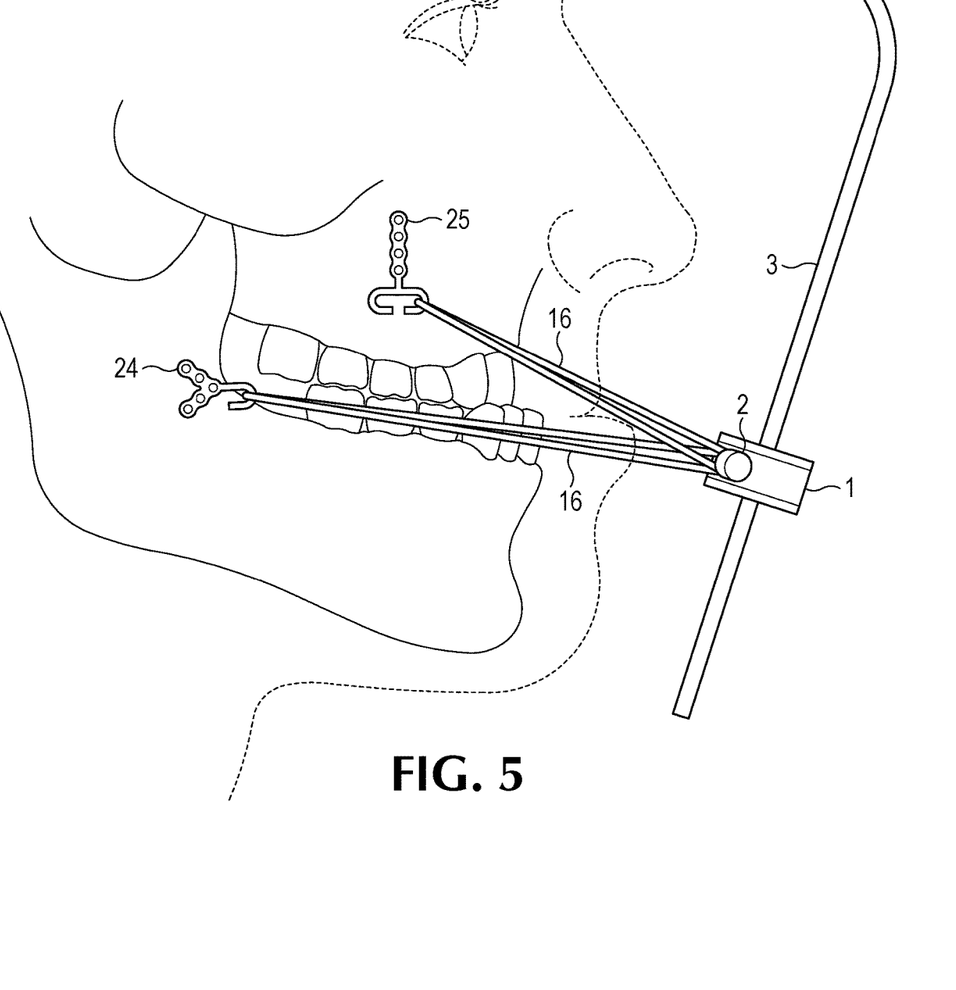
FIG. 5 is a plan side view of a portion of the face and airway developer of FIG. 1, showing the intraoral portion of an alternate embodiment, in its environment attached inside a patient's mouth.

The vertical position of the block 1 and horizontal bar 2 on the direction of the force delivery to the upper or lower jaws based on the clinical requirement for normalization of the facial structures for proper growth and airway structures for normalization of the patient's airway by advancing the mandible Referring to FIGS. 4a and 4b, device 110 further includes an intra-oral portion, including an intra-oral portion of straps 16, which are attached to anchors 15 of a maxillary anchoring assembly 23. In child patients, pulling on anchors 15 loosens the maxillary connection structures to the base of skull and causes a forward expansion of the upper jaw, which is highly desirable in patients with maxillary sagittal deficiency. By adjusting the force applied, the vertical growth of the maxilla can be encouraged, which is desirable in patients with vertical maxillary deficiency. Referring to FIG. 4b, maxillary anchoring assembly 23 includes screws 22, which are driven into the patient's palate. Screws 22 may be selectively removed on one side to provide a greater pulling force on the teeth on one side of the maxilla, than another. Side screws attached to the bone, make the maxillary bone on that side be pulled forward to take care of dental versus skeletal asymmetries. For example, if the patient's maxilla lacks bilateral symmetry, the left or the right side can be tightened to bone on the shorter side rather than on the other side, which is normal, to pull the short side more than the other. Also, if it is desired to pull more on the front of the maxilla, the frontmost screws 22 may be installed, rather than the rear screws 22. If the converse is desired the rear screws 22 may be installed, rather than the front screws. As shown in FIG. 4a, a set of straps 16 may be attached to mandible anchor 24. FIG. 5 shows a similar configuration, except for that assembly 23 is not shown, and a different form of maxillary anchor 25 is pulled by straps 16.

Figure 6:
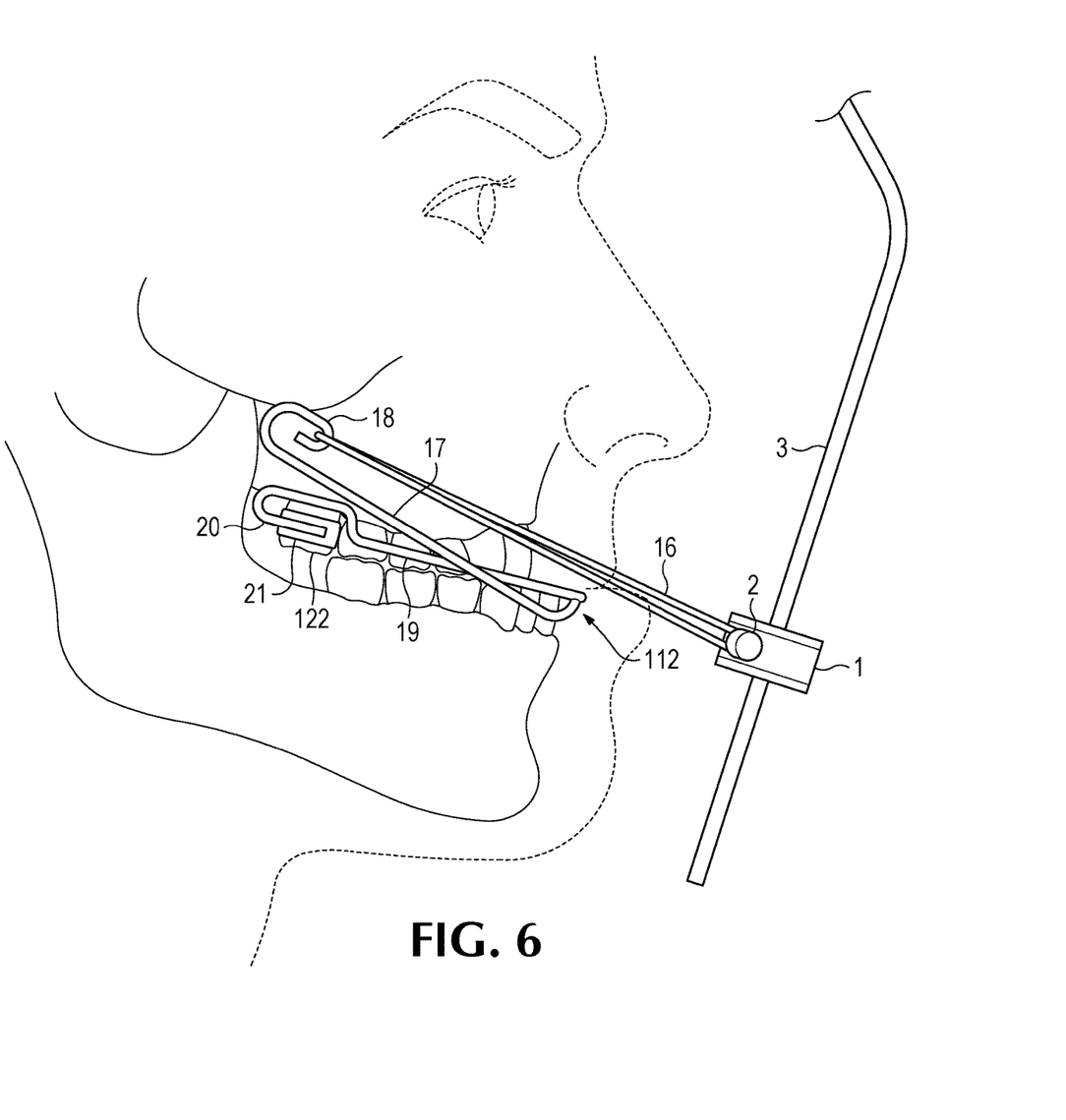
FIG. 6 is a plan side view of a portion of the face and airway developer of FIG. 1, showing the intraoral portion of another alternate embodiment designed to apply torque to an upper molar, in its environment attached inside a patient's mouth.

As shown in FIG. 6, a set of straps 16 pull on a structure 112, having an extra-oral and intra-oral portion, and designed to apply a vertical torque on a pair of upper molars 21. Straps connect to hooks 18 supported by extra-oral wing 17 (an equal bow 17 present on the other side of the face), which in turn is connected to intra-oral bow 19. Bow 19 bends at its ends 20, and each end is fit into a tube 21 that is connected to a molar 122. The forward pull on straps 16, causes a downward pull at the front of bow 19, which in turn provides a clockwise rotational force on molars 122 (in the plane of FIG. 6), accompanying the generally forward force, created by the pull of straps 16 (by way of bar 2 and bow 3). In a closely related embodiment extra-oral wings 17 are placed in an intra-oral position between the cheeks and the jaws.

Figure 7A:
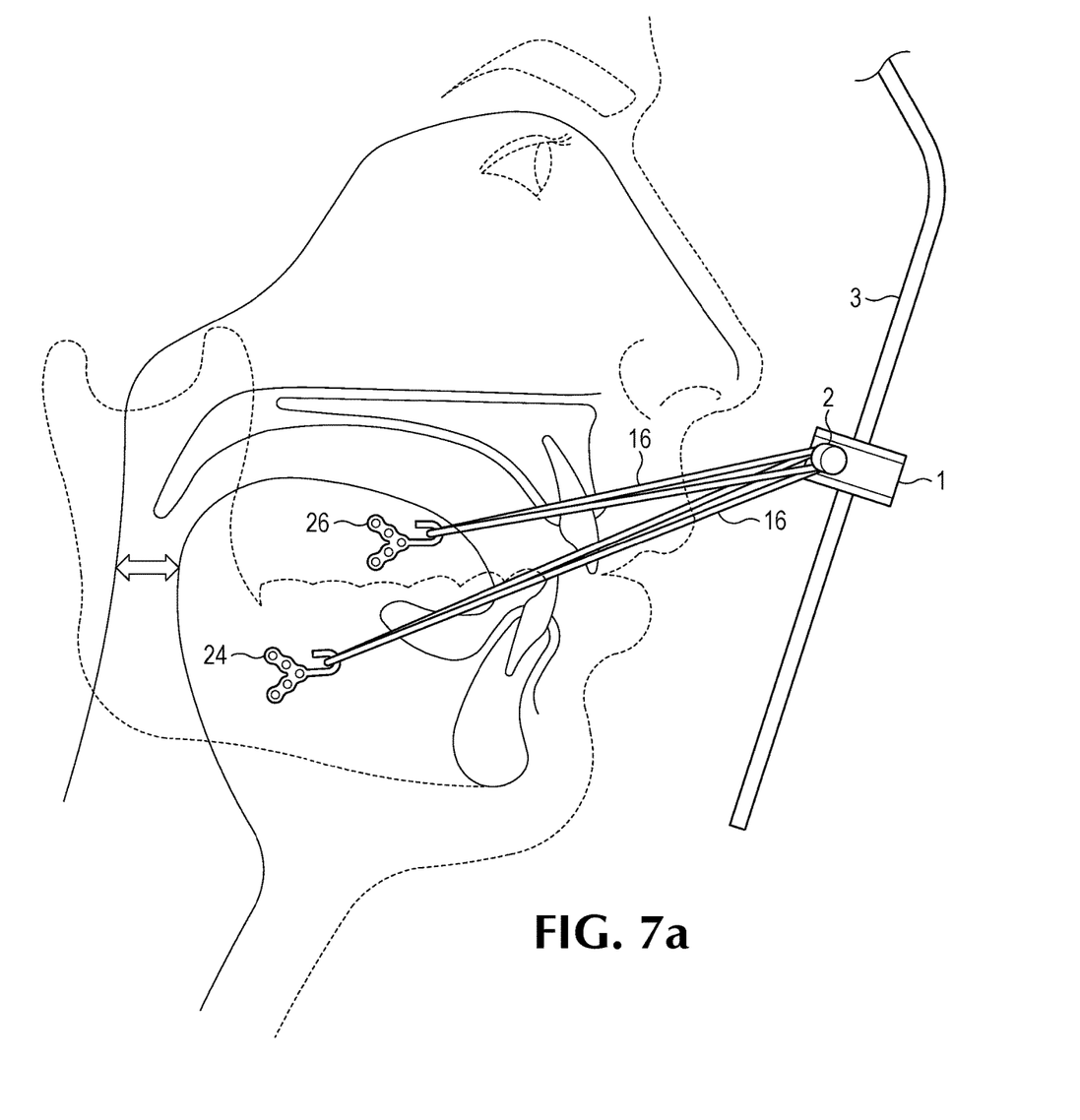
FIG. 7a is plan side view of a portion of the face and airway developer of FIG. 1, showing the intraoral portion of yet another alternate embodiment adapted to treat sleep apnea, in its environment attached inside a patient's mouth to the lower jaw and tongue.
Figure 7B:
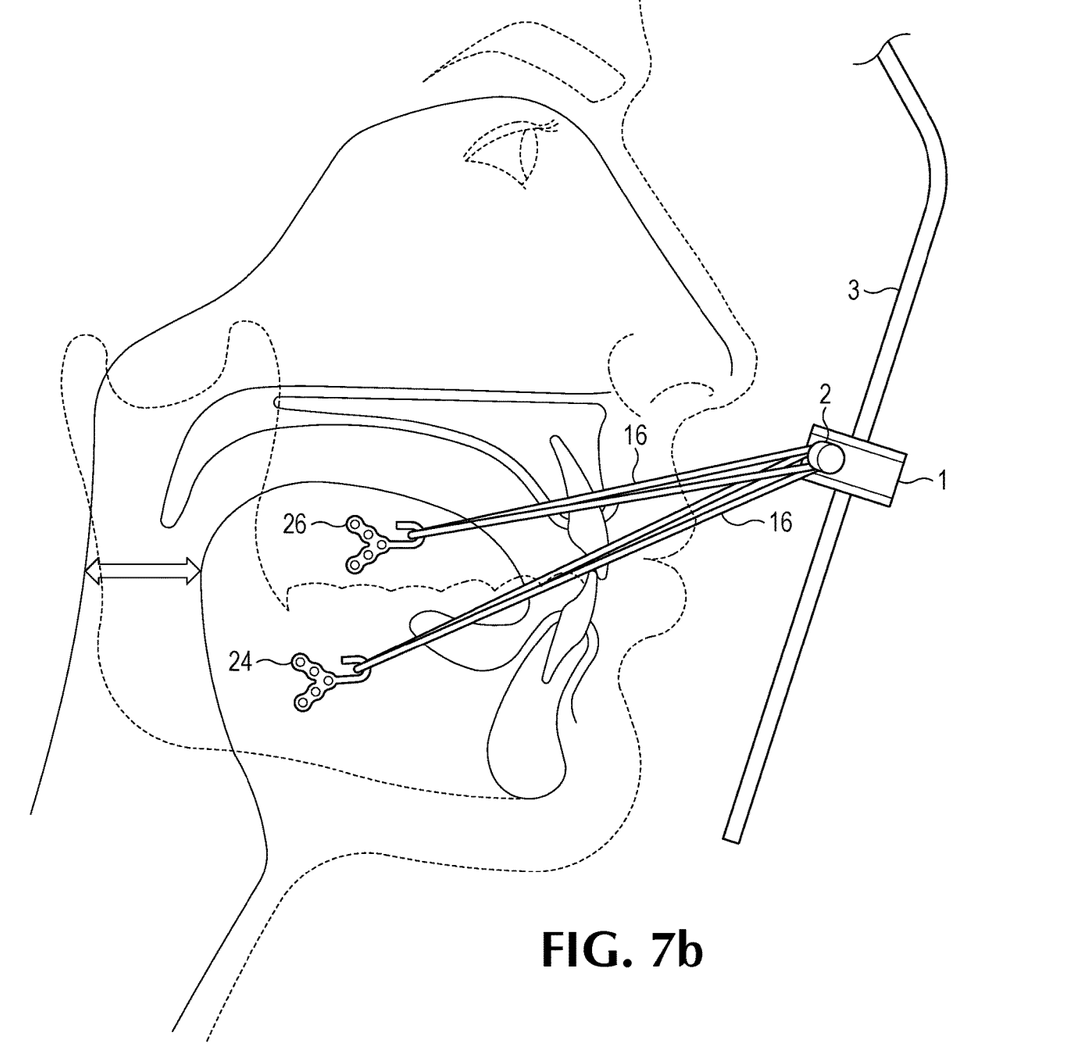
FIG. 7b is a plan view of the appliance of FIG. 7a, with the tongue and lower jaw pulled forward to open the airway.
Figure 8A:
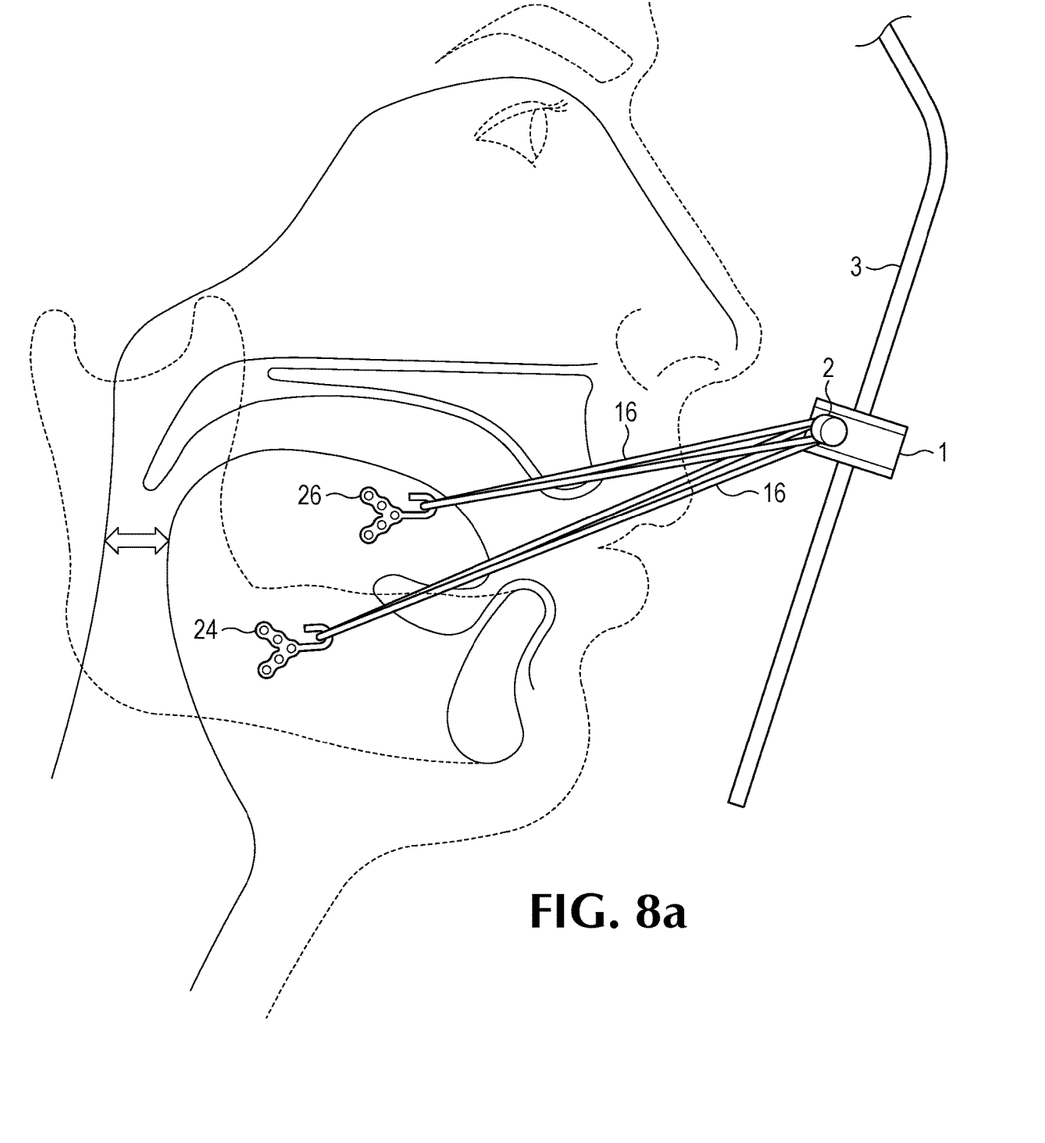
FIGS. 8a and 8b show the appliance of FIGS. 7a and 7b, but in an environment attached inside the mouth of a patient lacking teeth.
Figure 8B:
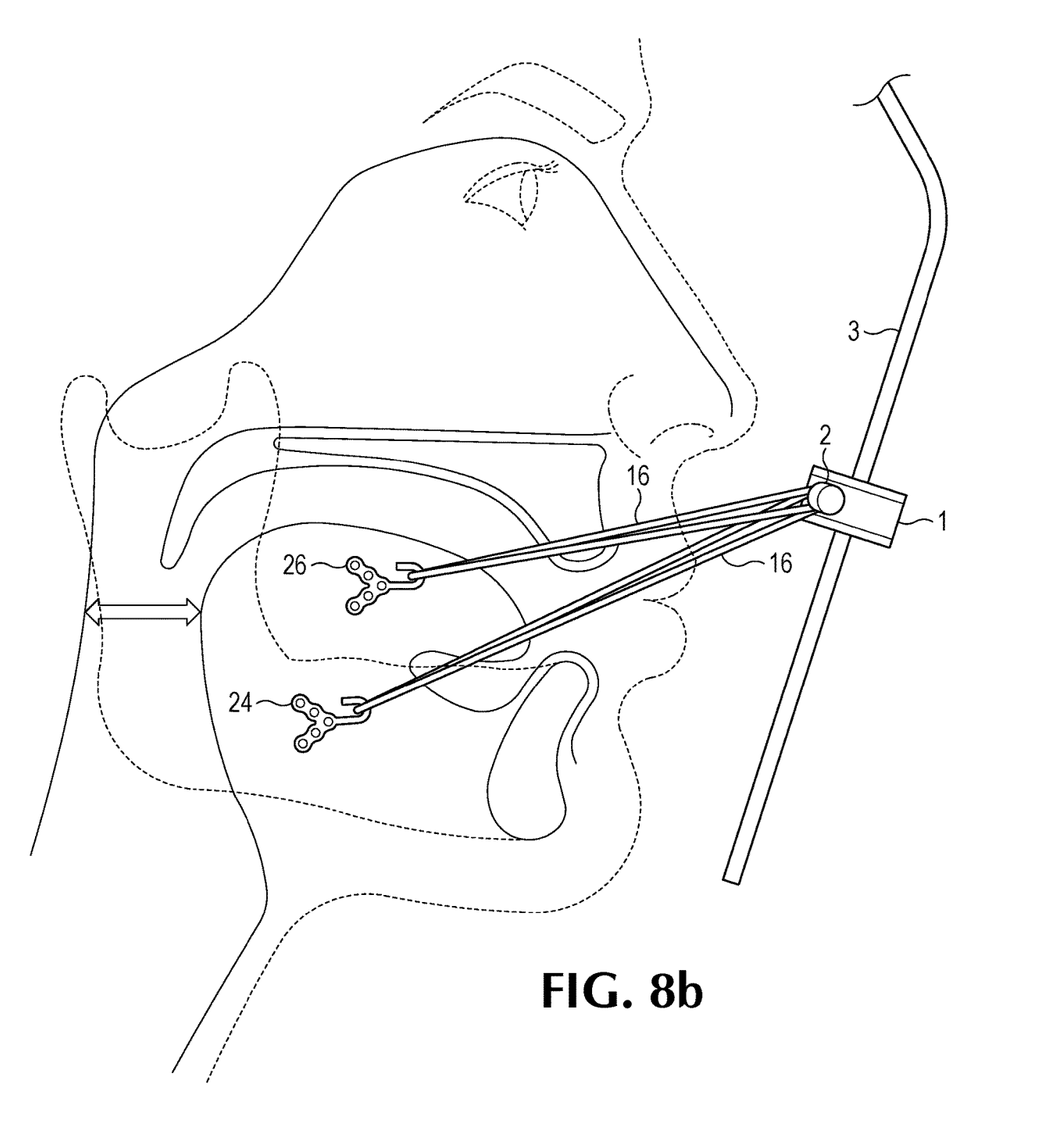

FIGS. 7a and 7b show a system in which the straps 16 are used to pull the tongue (by way of anchor 26) and the lower jaw (by way of anchor 24) forward, for the treatment of small jaws in children or sleep apnea in children or adults. FIGS. 8a and 8b show the same system but attached in a patient without teeth.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A method for treating a patient's sleep disordered breathing, the method comprising:
   placing a fulcrum of an appliance on a forehead of the patient, wherein the appliance comprises:
      an extra-oral portion comprising a lever including the fulcrum and a rigid lever arm slidingly attached to the fulcrum, wherein the rigid lever arm has a first end disposed above the fulcrum and a second end disposed below the fulcrum, wherein the extra-oral portion further includes a headstrap set attached to the rigid lever arm at a first location disposed above the fulcrum and adjacent to the first end; and
      an intra-oral strap assembly connected to the rigid lever arm at a second location disposed below the fulcrum and adjacent to the second end of the rigid lever arm;
   placing the headstrap set about a top portion of the head of the patient;
   attaching the intra-oral strap assembly to an intra-oral feature of the patient; and
   forcing the second end and the second location of the rigid lever arm away from the head by adjusting the headstrap set to pull on the first location of the rigid lever arm disposed above the fulcrum, such that the intra-oral strap assembly is placed into tension to pull on the intra-oral feature of the patient.

2. The method of claim 1, wherein said intra-oral feature is said patient's tongue.

3. The method of claim 2, wherein said intra-oral strap assembly is also attached to said patient's lower teeth.

4. The method of claim 1, wherein said intra-oral feature is said patient's lower teeth.

5. The method of claim 1, wherein said intra-oral feature is said patient's lower jaw.

6. The method of claim 1, wherein said headstrap set is attached to said lever arm by means of a top block that is slidingly engaged to said lever arm.

7. The method of claim 6, wherein a set screw is engaged to said top block to fix the position of said top block on said lever arm.

8. The method of claim 7, further including adjusting the position of said top block on said lever arm and fixing it in place with said set screw.

9. The method of claim 1, wherein said intra-oral strap assembly is connected to said lever arm by means of a bottom block.

10. The method of claim 9, wherein a set screw is engaged to said bottom block to fix the position of said bottom block on said lever arm.

11. The method of claim 1, wherein said headstrap set having a left and right side including a bow on both said left and right sides, each bow having a hook, and said head strap set further having a headstrap, and wherein said headstrap defines at least one hole for each one of said hooks, and wherein each of said hooks is engages with a said hole.

12. The method of claim 11, wherein said headstrap defines a set of holes for each one of said hooks, so that a user may select a hole to attach each said hook to, thereby constituting a further adjustment.

13. A method for treating a patient's sleep disordered breathing, the method comprising:
   placing a fulcrum of an appliance on a forehead of the patient, wherein the appliance comprises:
      an extra-oral portion comprising a type 1 lever including the fulcrum and a rigid lever arm slidingly attached to the fulcrum, wherein the rigid lever arm has a first end and a second end opposite the first end, wherein the extra-oral portion further includes a headstrap set attached to the rigid lever arm at a first location disposed above the fulcrum adjacent to the first end; and
      an intra-oral strap assembly connected to the rigid lever arm at a second location disposed adjacent to the second end of the rigid lever arm below the fulcrum;
   placing the headstrap set about a top portion of the head of the patient;
   attaching the intra-oral strap assembly to an intra-oral feature of the patient; and
   forcing the second end and the second location of the rigid lever arm away from the head by adjusting the headstrap set to pull on the first location of the rigid lever arm, such that the intra-oral strap assembly pulls on the intra-oral feature of the patient.

\* \* \* \* \*

UNITED STATES PATENT AND TRADEMARK OFFICE
CERTIFICATE OF CORRECTION

PATENT NO. : 12,274,596 B1  
APPLICATION NO. : 16/729551  
DATED : April 15, 2025  
INVENTOR(S) : Joseph Yousefian Page 1 of 1

It is certified that error appears in the above-identified patent and that said Letters Patent is hereby corrected as shown below:

In the Claims

Claim 11, Column 6, Line 9, the text "and said head strap" should read --and said headstrap--.

Signed and Sealed this  
Thirteenth Day of May, 2025

Coke Morgan Stewart  
*Acting Director of the United States Patent and Trademark Office*